(12) United States Patent
Hogan

(10) Patent No.: US 9,888,841 B2
(45) Date of Patent: Feb. 13, 2018

(54) HEAD-MOUNTED OPTICAL COHERENCE TOMOGRAPHY

(71) Applicant: Joshua Noel Hogan, Los Altos, CA (US)

(72) Inventor: Joshua Noel Hogan, Los Altos, CA (US)

(*) Notice: Subject to any disclaimer, the term of this patent is extended or adjusted under 35 U.S.C. 154(b) by 0 days.

(21) Appl. No.: 14/910,442

(22) PCT Filed: Aug. 9, 2014

(86) PCT No.: PCT/US2014/050457
§ 371 (c)(1),
(2) Date: Feb. 5, 2016

(87) PCT Pub. No.: WO2015/023547
PCT Pub. Date: Feb. 19, 2015

(65) Prior Publication Data
US 2016/0174835 A1 Jun. 23, 2016

Related U.S. Application Data

(60) Provisional application No. 61/864,556, filed on Aug. 10, 2013.

(51) Int. Cl.
*A61B 3/10* (2006.01)
*A61B 3/00* (2006.01)
*A61B 3/14* (2006.01)
*A61B 3/02* (2006.01)
*G02B 27/00* (2006.01)

(52) U.S. Cl.
CPC ............ *A61B 3/102* (2013.01); *A61B 3/0025* (2013.01); *A61B 3/0091* (2013.01); *A61B 3/1005* (2013.01); *G02B 27/0068* (2013.01)

(58) Field of Classification Search
CPC ........... A61B 3/103; A61B 3/14; A61B 3/113; A61B 3/152; A61B 3/1225; A61B 3/1015
USPC ........ 351/221, 205–206, 210, 200, 246, 208
See application file for complete search history.

(56) References Cited

U.S. PATENT DOCUMENTS

2009/0244485 A1* 10/2009 Walsh ................... A61B 3/102
351/221
2011/0228221 A1* 9/2011 Hanebuchi ............ A61B 3/102
351/206

* cited by examiner

*Primary Examiner* — Dawayne A Pinkney

(57) ABSTRACT

The invention provides a system and method for obtaining ophthalmic measurements whereby the inventive device is configured to be head mountable, automatically axially length aligned with a selected target, and laterally aligned so that light from an OCT source enters through the pupil of the eye under test. The frame of the head mountable OCT is customizable, capable of analyzing both the left and right eye of a subject. The inventive device can be operated by the person undergoing test. Embodiments include mechanisms for eye fixation, lateral, angular and depth scanning of target regions. A variety of embodiments are taught, including the scanning of both eyes of a subject at substantially the same time, and a configuration of a photonic module coupleable with a plurality of frames. Embodiments include a variety of OCT sources, such as MRO, swept source, time domain, and spectral domain.

3 Claims, 9 Drawing Sheets

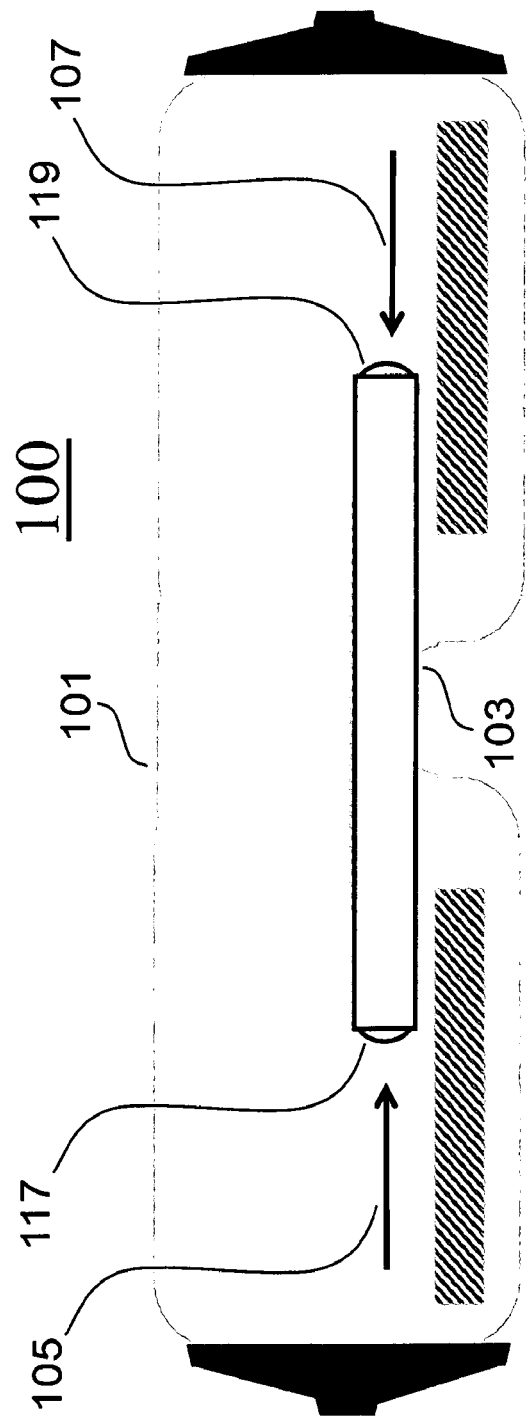
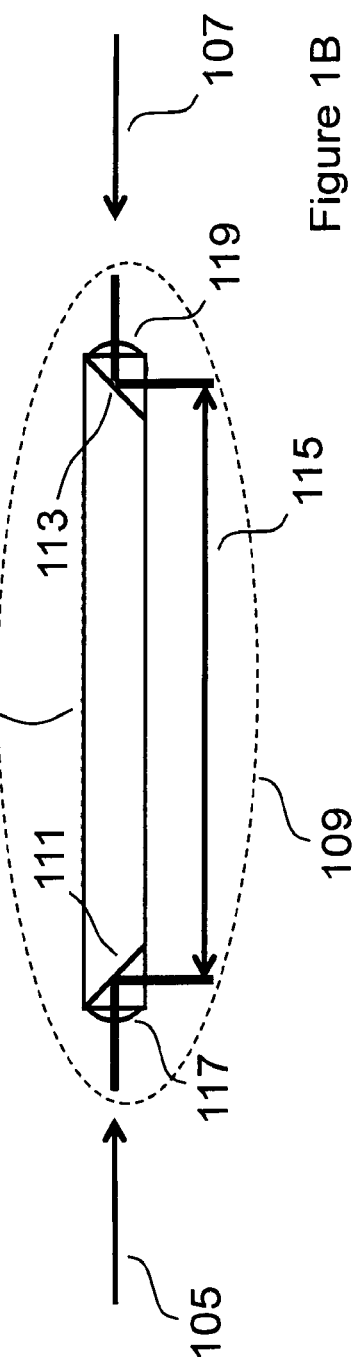

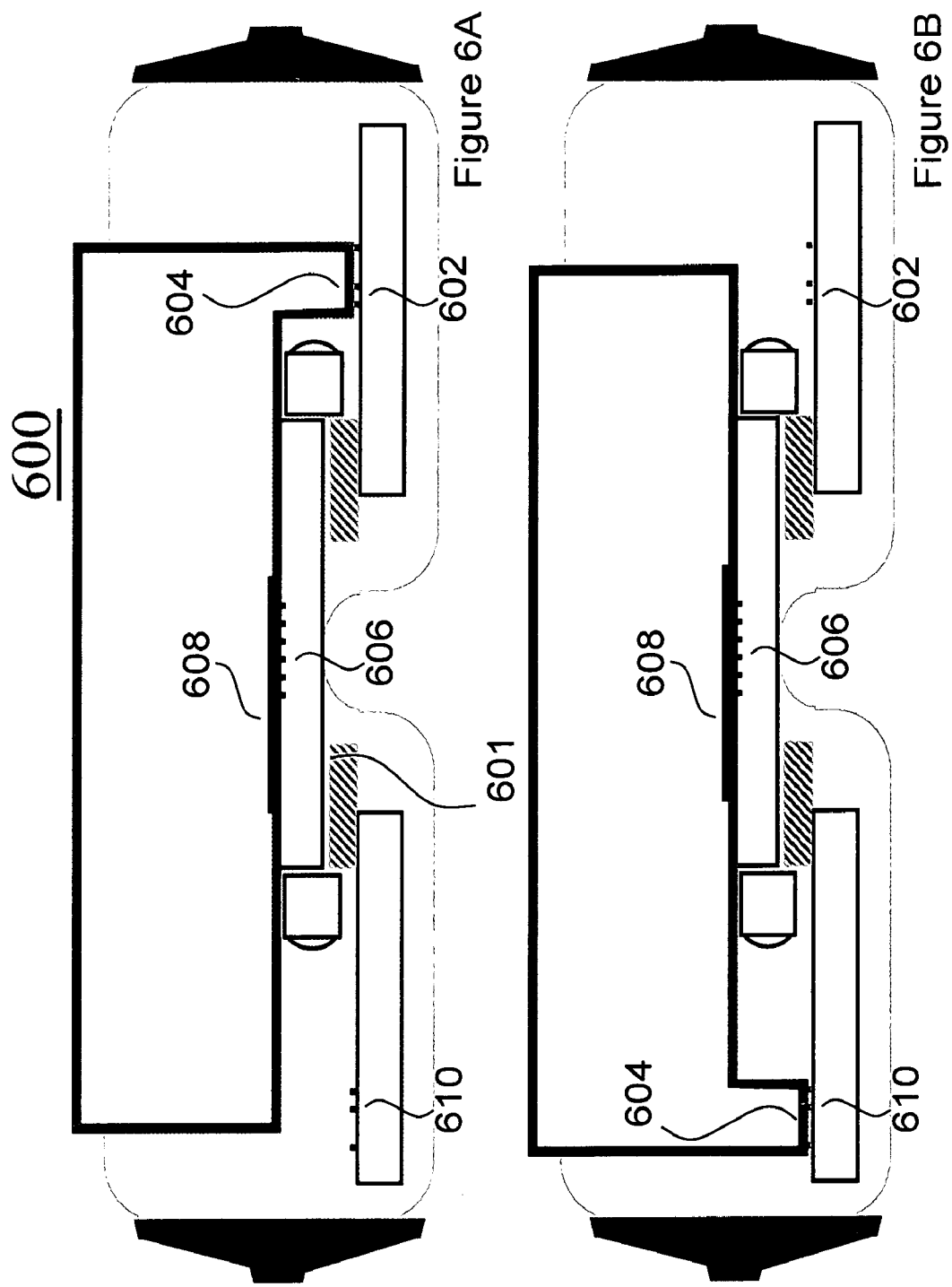

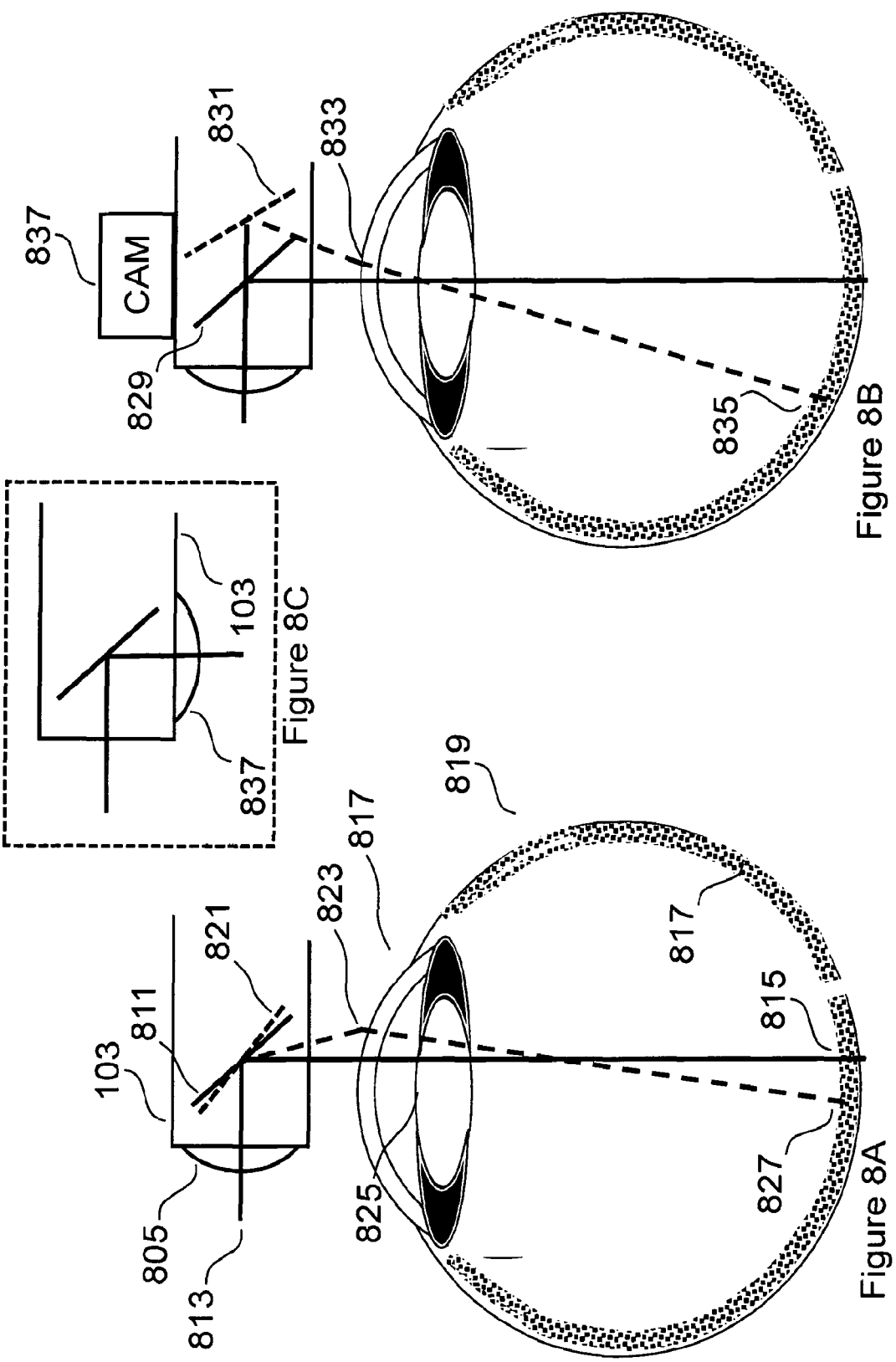

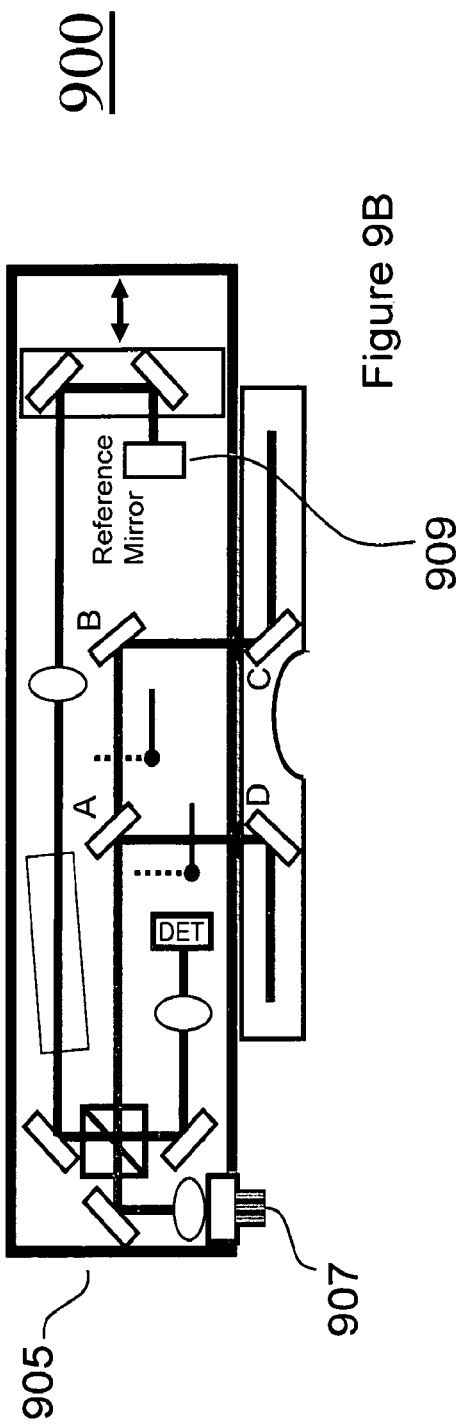
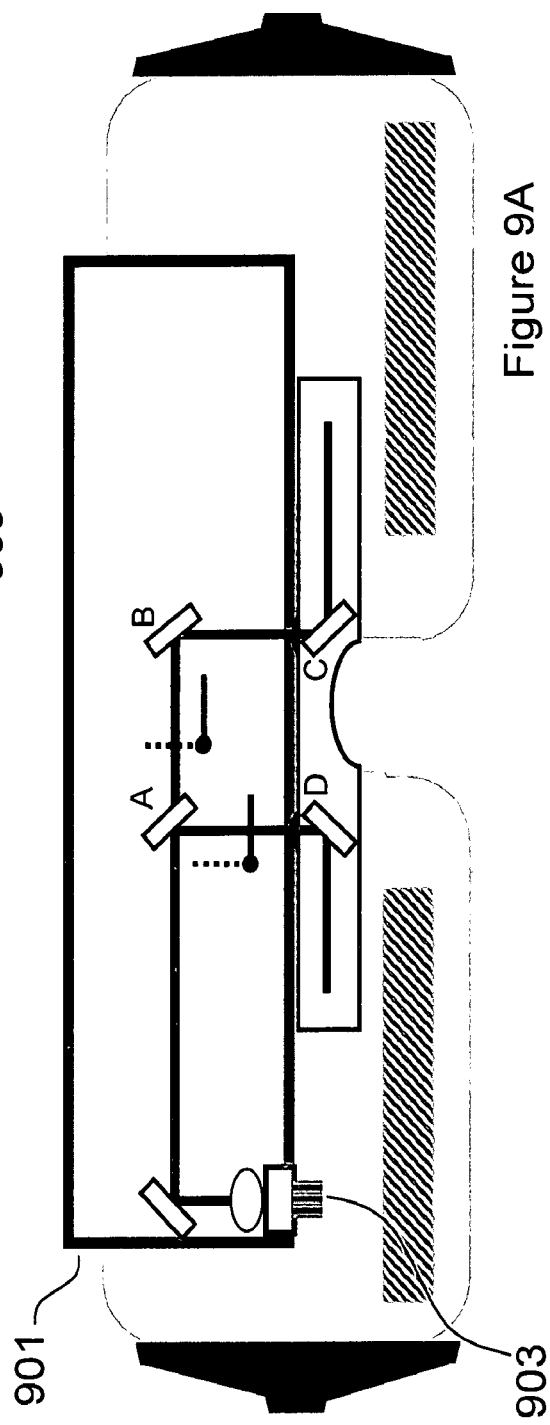
Figure 9B
Figure 9A

HEAD-MOUNTED OPTICAL COHERENCE TOMOGRAPHY

CROSS REFERENCES TO RELATED PATENTS OR APPLICATIONS

This patent application, docket number CI130701PT, is related to U.S. Pat. No. 7,526,329 titled "Multiple Reference Non-invasive Analysis System" and U.S. Pat. No. 7,751,862 titled "Frequency Resolved Imaging System", the contents of both of which are incorporated herein as if fully set forth herein. This patent application is also related to the following three patent applications, all of which were filed on Nov. 3, 2012: PCT patent application number PCT/US2012/063471 titled "Improved Correlation of Concurrent Non-invasively Acquired Signals"; patent application Ser. No. 13,668,261 titled "A Field of Light based Device"; and patent application Ser. No. 13,668,258 titled "Non-invasive Optical Monitoring"; the contents of all of which are incorporated herein as if fully set forth herein.

FIELD OF THE INVENTION

The invention described and illustrated in this application relates to non-invasive imaging and analysis techniques such as Optical Coherence Tomography (OCT). In particular it relates the use of OCT systems to make in-vivo measurements of aspects of an eye. Such OCT systems include, but are not limited to, the multiple reference OCT systems, referred to as an MRO system, that is described in U.S. Pat. Nos. 7,751,862 and 7,526,329.

BACKGROUND OF THE INVENTION

Non-invasive imaging and analysis of targets is a valuable technique for acquiring information about systems or targets without undesirable side effects, such as damaging the target or system being analyzed. In the case of analyzing living entities, such as human tissue, undesirable side effects of invasive analysis include the risk of infection along with pain and discomfort associated with the invasive process.

Optical coherence tomography (OCT) is a technology for non-invasive imaging and analysis. There exists more than one OCT technique. Time Domain OCT (TD-OCT) typically uses a broadband optical source with a short coherence length, such as a super-luminescent diode (SLD), to probe and analyze or image a target. Multiple Reference OCT (MRO) is a version of TD-OCT that uses multiple reference signals. Another OCT technique is Fourier Domain OCT (FD-OCT). A version of Fourier Domain OCT, called Swept Source OCT (SS-OCT), typically uses a narrow band laser optical source whose frequency (or wavelength) is swept (or varied) over a broad wavelength range. In TD-OCT systems the bandwidth of the broadband optical source determines the depth resolution. In SS-OCT systems, depth the wavelength range over which the optical source is swept determines the depth resolution. Another variation of FD-OCT is spectral domain where the detection process separates wavelengths by means of a spectrometer.

TD-OCT technology operates by applying probe radiation from the optical source to the target and interferometrically combining back-scattered probe radiation from the target with reference radiation also derived from the optical source. The typical TD-OCT technique involves splitting the output beam into probe and reference beams, typically by means of a beam-splitter, such as a pellicle, a beam-splitter cube, or a fiber coupler. The probe beam is applied to the target. Light or radiation is scattered by the target, some of which is back-scattered to form a back-scattered probe beam, herein referred to as signal radiation.

The reference beam is typically reflected back to the beam-splitter by a mirror. Light scattered back from the target is combined with the reference beam, also referred to as reference radiation, by the beam-splitter to form co-propagating reference radiation and signal radiation. Because of the short coherence length, only light that is scattered from a depth within the target whose optical path length is substantially equal to the path length to the reference mirror can generate a meaningful interferometric signal.

Thus the interferometric signal provides a measurement of scattering properties at a particular depth within the target. In a conventional TD-OCT system, a measurement of the scattering values at various depths can be determined by varying the magnitude of the reference path length, typically by moving the reference mirror. In this manner the scattering value as a function of depth can be determined, producing a depth scan of the target.

Various techniques exist for varying the magnitude of the reference path length. Electro-mechanical voice coil actuators can have considerable scanning range, however, there are problems with maintaining stability or pointing accuracy of a reference mirror. Fiber based systems using fiber stretchers have speed limitations and have size and polarization issues. Rotating diffraction gratings can run at higher speeds, but are alignment sensitive and have size issues.

Piezo devices can achieve high speed scanning and can have high pointing accuracy, however to achieve a large scanning range requires expensive control systems and such systems have limited speed. A scanning method that effectively amplifies the scan range of a piezo device is described in the U.S. Pat. Nos. 7,526,329 and 7,751,862 referenced hereinabove.

The technique described in these publications uses multiple reference signals with increasing scan range and correspondingly increasing frequency interference signals. This scanning method can achieve large scan range at high speed with good pointing stability. The interference signals associated with the multiple reference signals are detected by a single detector as a complex signal consisting of the combined interference signals.

In swept source Fourier domain OCT systems depth scanning is accomplished by repeatedly sweeping the wavelength of the optical source. The wavelength range over which the optical source is swept determines the depth resolution. The period of the sweep repetition rate determines the period of the depth scans.

In addition to depth scanning, lateral scanning of a target is required for many imaging and analysis applications. Some conventional techniques for lateral scanning use stepper or linear motors to move the OCT scanning system. In some applications angular scanning is accomplished by electro-mechanical oscillating mirrors, typically referred to as galvo-scanners, which angularly deviate the probe beam.

Currently available OCT systems are bulky, weighty, complex and high cost. Currently available OCT systems have complex and bulky alignment and scanning sub-systems that result in physically large and costly systems. Moreover, in typical ophthalmic applications currently available OCT systems must be operated by a trained physician or technician. What is needed is a lightweight, robust, reliable monitoring device that is amenable to alignment by a layperson, and provides reliable and accurate measurements.

Furthermore, ophthalmic applications, such as retinal examination, often require the retina to be at a fixed orientation with respect to the OCT probe beam or with respect to the scanning region of the OCT probe beam. This process is also referred to as "fixation" of the eye. Currently available OCT systems that require fixation at locations other than the location being analyzed by the OCT beam also require a complex fixation mechanism.

Major causes of blindness are macular degeneration and diabetic retinopathy. Both of these conditions can benefit from timely medical intervention. People who are at risk of eye damage from these conditions need frequent monitoring because occurrence of an adverse situation (for example the growth of weak and leaky blood vessels), if not addressed in a timely manner, can cause irreversible damage to the retina leading inexorably to loss of vision.

Current practice involves monthly visits to a doctor. Many of these visits are wasteful if nothing has changed and in the case of a change, significant irreversible damage can occur within a month. Therefore, reducing the time between retinal measurements without being wasteful is advantageous.

In the retina of an eye, both the vascular system and the central nervous system are accessible for non-invasive analysis by an OCT system. This provides the opportunity to monitor for the onset or progression of a myriad of conditions, in addition to macular degeneration and diabetic retinopathy. Frequent monitoring of such conditions would be facilitated by a low cost system capable of making the required measurements without the aid of a trained professional.

There is therefore an unmet need for a low cost OCT system capable of making in-vivo OCT measurements of an eye, where such a system has automatic alignment, scanning and fixation mechanisms that do not need a trained operator and can preferably be operated by the subject him or herself. What is also needed is a system that communicates scan results to a medical professional.

SUMMARY OF THE INVENTION

The invention taught herein meets at least all of the aforementioned unmet needs. The invention provides a method, apparatus and system that has fixed coarse alignment and automatic fine alignment of an OCT system with respect to an eye. In some embodiments the system also provides a scan of a desired region and uses a flexible fixation technique.

In the preferred embodiment, a photonic module attaches to a frame that fits on a subject's head in a manner that may be similar to a pair of spectacles. The frame is selected such that, when attached to the frame, the photonic module is at least coarsely aligned with at least one of the subject's eyes and such that the OCT scanning region is at least coarsely aligned with the retina of the eye, i.e. is aligned with the axial length of the eye.

In the preferred embodiment the frame includes a turning mirror that directs the OCT beam into the Subject's eye. In alternate embodiments one or more corrective lenses compensate for refractive error of the Subject's eye(s). In further alternate embodiments, the corrective lens is adjustable, either manually or by electronic control. Such adjustable lenses are referred to as configurable corrective lenses.

In the preferred embodiment the photonic module includes a movable component that enables dynamic fine axial length adjustment. This fine axial length adjustment is performed using feedback from the processed OCT depth scans of the retina.

In the preferred embodiment the photonic module can be attached to either side (right or left) of the frame in a manner that coarsely aligns the photonic module with respect to the location of the center of the front of the target eye, and with respect to the axial length of the target eye, and with respect to the refractive error of the target eye. The ability to be attached to either side of the frame enables the system to measure aspects of either eye in turn. Other embodiments enable measuring both of a subject's eyes without moving the module.

In an alternate embodiment, the turning mirror that directs the OCT beam into the Subject's eye is angularly adjustable to enable pointing to a particular locality of the retina or a selected set of localities of the retina or to enable scanning a particular region of the retina of the eye.

In an alternate embodiment, the turning mirror that directs the OCT beam into the Subject's eye is angularly adjustable to enable fixation techniques that facilitate pointing to one or more localities or scanning a particular region of the retina. Fixation techniques include using the OCT probe beam as the fixation signal or using a visible beam at a wavelength different from the wavelength of the OCT probe beam. In a further embodiment the system includes a camera.

BRIEF DESCRIPTION OF THE DRAWINGS

The drawings to aid in understanding the invention are:

FIGS. 1, 1A and 1B inclusive, is a schematic type illustration, front view, of a frame comprised of two components: a first component, in many respects similar to a conventional pair of eye glasses (or spectacles) that fit the particular subject wearing the frame; and a second component that contains two 45 degree mirrors that direct light beams towards the eyes of the subject wearing the frame (depicted in FIG. 1B, at a 90 degree rotation).

FIGS. 5, 5A, 5B and 5C inclusive, depicts an alternate embodiment wherein targets in both eyes can be measured without repositioning the OCT photonic module on the frame.

FIGS. 6, 6A and 6B inclusive, depicts an embodiment providing magnetic connectors to join the OCT photonic module and the frame, and providing coarse axial alignment by placement of the connectors.

FIGS. 8, 8A and 8B inclusive, depict an embodiment providing angular scanning by means of adjustable mirrors where 8B has extended scanning capability by including a linear translation capability to keep the beam substantially centered on the pupil. FIG. 8B also depicts an optional camera to monitor the eye. FIG. 8C depicts an alternate location for a corrective lens.

FIGS. 9, 9A and 9B inclusive, depicts an embodiment where the photonic module uses an external fiber-coupled OCT system and an embodiment where the photonic module uses an external optical swept source.

DETAILED DESCRIPTION OF A PREFERRED EMBODIMENT

Figure 2:
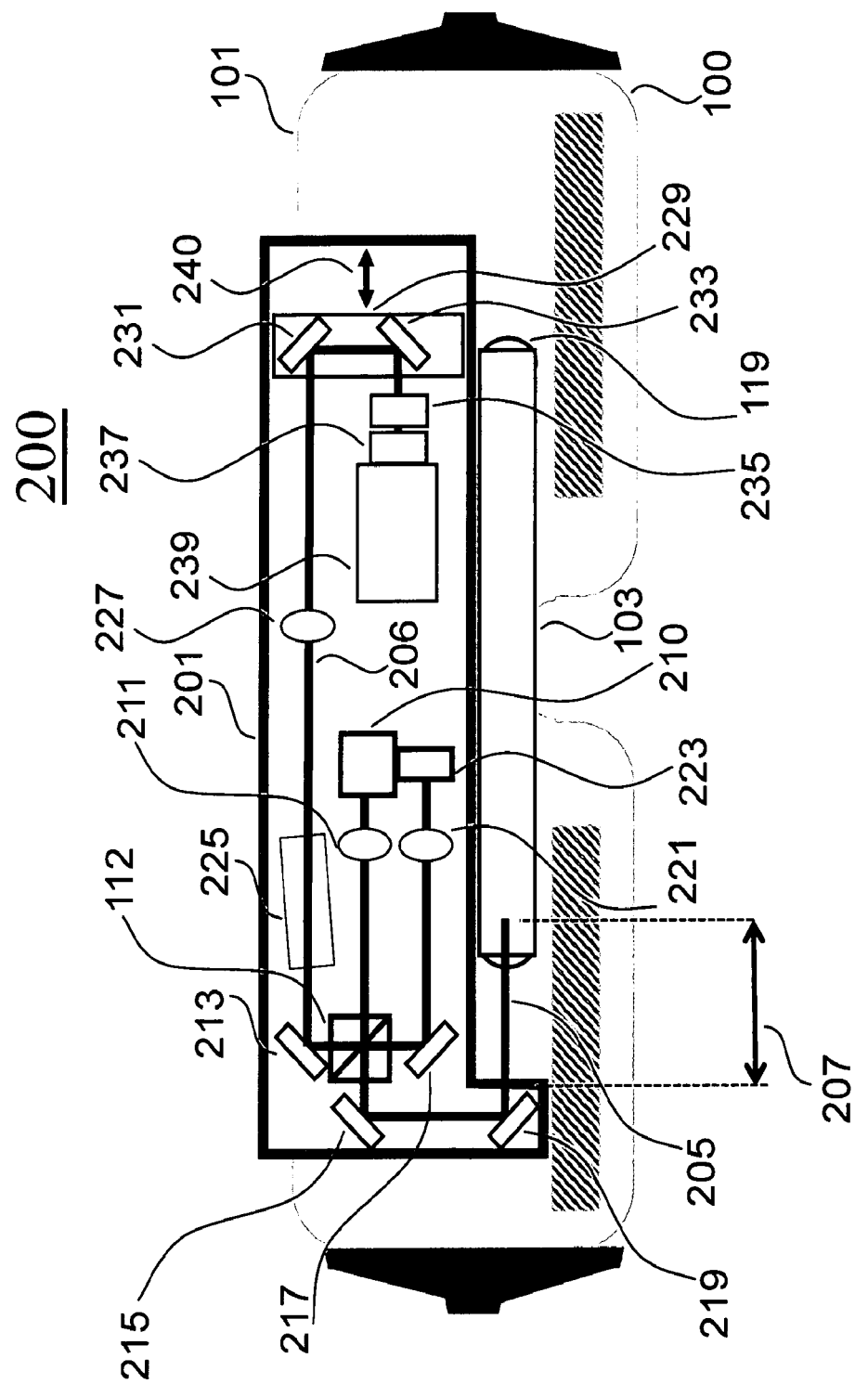
FIG. 2 depicts the OCT photonic module attached to the frame such that the probe beam of the OCT photonic module will enter the target eye with correct lateral alignment.

The invention taught herein includes a device and method of non-invasively measuring aspects of a component of an eye. Such components include, but are not limited to, the retina of an eye. Such aspects include, but are not limited to: the thickness of the retina at a particular location; the thickness of the retina at a set of locations; a depth scan of the retina at one or more locations; a two dimensional scan of a region of the retina where one dimension is depth.

In the preferred embodiment, an OCT photonic module directs a light beam, referred to as a probe beam, into the eye and captures at least a portion of the light that is scattered back towards the OCT photonic module. This back-scattered light is combined with reference light to form one or more interference signals that can be processed to a yield depth scan of the retina.

In the preferred embodiment a frame is configured to fit a particular Subject (or set of subjects) whose eye is the target eye to be measured much in the manner that a pair of spectacles is fitted to a person. The frame is further configured so as to be laterally aligned with the target eye such that the probe beam of the OCT photonic module will be directed into the target eye through its pupil. As used herein, "laterally aligned" refers to aligning in a direction orthogonal to the probe beam entering the eye, also referred to as aligning in a lateral direction.

Note regarding numbering in the Figures: components remaining constant from one Figure to another are, where possible, given the same number as in a preceding Figure. Where the only difference is the addition or substitution of components, only components not previously appearing are numbered and discussed. In cases of the configuration of the OCT photonic module, taking into account that OCT is well understood, it is opined that those of average skill in the relevant art will find the Figures illustrative, and an aid to understanding the invention.

FIG. 1 depicts a frame 100 according to the invention, wherein a first component 101 is in many respects similar to a conventional pair of eyeglasses (or spectacles) that fit the particular subject. A second component 103 contains two (a first and a second) 45 degree mirrors, 113 that direct light beams traveling in the paths 105 and 107 towards the Subject wearing the frame 100 (i.e. referred to herein variously as frame-wearer, User, Subject, Subject under test). These 45-degree mirrors are commonly referred to as turning mirrors and are fixed at 45 degrees in some embodiments and in other embodiments are angularly adjustable for pointing or scanning.

FIG. 1B depicts the second component 103 in a 90-degree rotated view 109. FIG. 1B shows a first and a second 45-degree mirror 111 and 113 respectively. The separation 115 between the two 45 degree mirrors 111 and 113 is configured to be the nominal lateral distance between the pupils of the subject's eyes. FIG. 1B also shows light paths—a first probe path 105 and a second probe path 107, beams of light (probe beams from the OCT photonic module, discussed in FIG. 2 below) each traveling toward one of the 45-degree mirrors (111 and 113) and then directed toward an eye under test.

The second component 103, in an alternate embodiment, includes one or two lenses, depicted as a first and a second curved surface 117 and 119 (also referred to herein as "corrective" lenses). Such optional lenses may be convex or concave and are selected to compensate for aberration errors in the target eyes, similar to the manner in which, for example, corrective lenses correct for distance vision. It can be appreciated that in the case where the invention is "customized" for a particular subject or eye patient, inclusion of corrective lenses is an aspect of such customization.

The second component 103 is oriented upon, or, in some embodiments, affixed to the first component 101 such that the two 45 degree mirrors 111 and 113 are in front of and centered on the pupils of the left and right eye of the subject. Thus, the first component 101 and the second component 103 together form a frame 100 that is placed anterior to the eyes of a subject and is aligned with the eyes of the subject, where at least one of the eyes is a target eye to be measured or scanned. It can be appreciated that while the preferred embodiment is an eyeglass-like frame, many versions of head-mounting are envisioned, wherein the positioning of the second component provides for directing of the OCT beams onto the target region of the subject's eye or eyes. For example, if weight is a concern, a helmet like device is an alternate embodiment.

FIG. 2 depicts a head mountable OCT device 200 according to the invention; the frame 100 of FIG. 1, comprised of a first component 101 and a second component 103, with an OCT photonic module 201 attached to the frame such that the probe beam 205 of the OCT photonic module, traveling along the path 105 of FIG. 1 strikes a second 45 degree mirror 113 and enters the target eye (not shown) with correct lateral alignment.

The OCT photonic module 201 includes a source 210 that generates radiation directed by a configuration of lenses, mirrors and beam-splitter to probe radiation 205, making a round-trip along pathway 105 (in FIG. 1) from the target and back to the detector 223, or reference radiation, making a round-trip to the reference mirror 337 and the detector 223 along pathway 206. Radiation from the source 210 passes through a first lens 211 (typically a collimating lens) and then to a beam-splitter 212. Probe radiation exits the beam-splitter 212, encounters a second turning mirror 215, a fourth tuning mirror 219, exits though the probe beam output port [not shown] in the photonic module to a first 45 degree turning mirror 111, and proceeds to enter the target eye.

Figure 3:
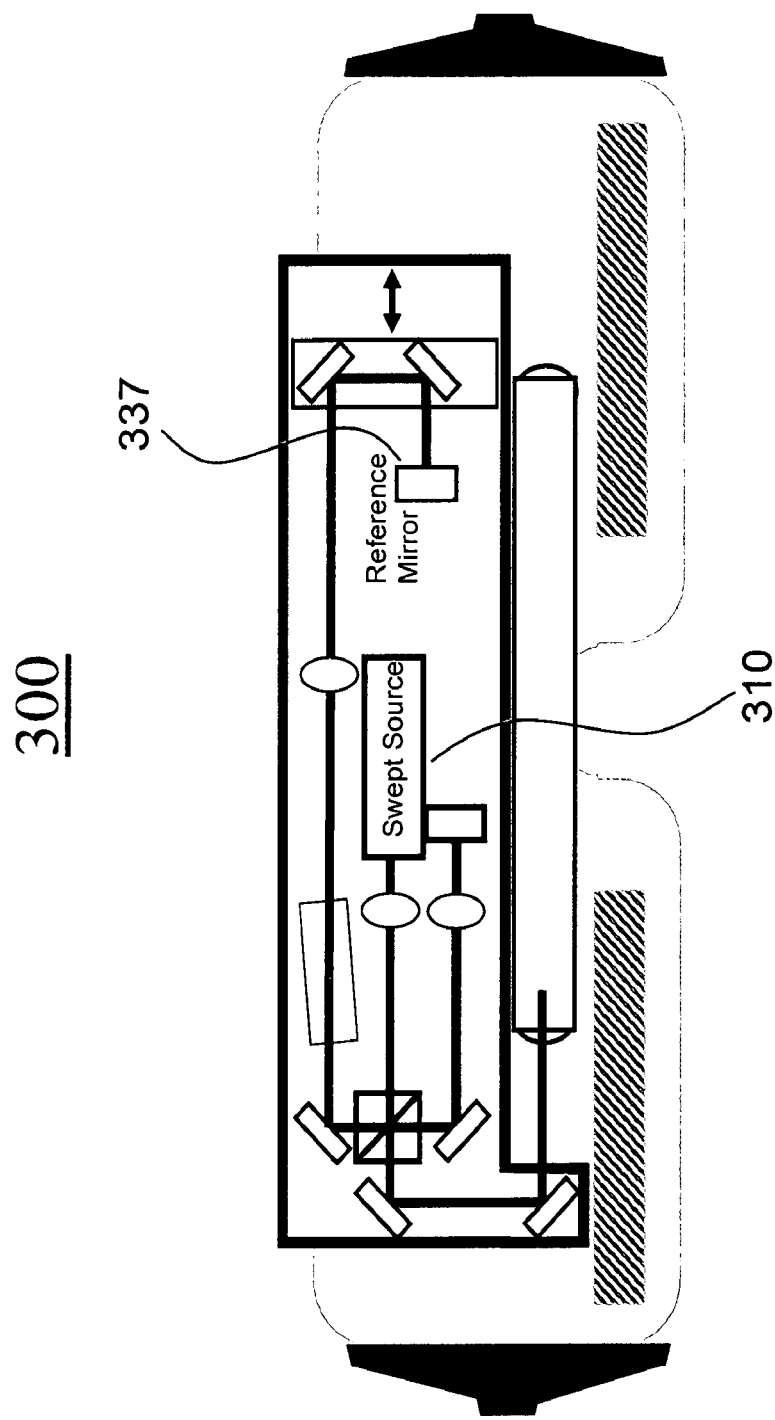
FIG. 3 depicts an alternate embodiment of the OCT photonic module of FIG. 2, using a swept source.

Reference radiation proceeds from the beam-splitter 212 to a first turning mirror 213 along reference path 206 passing through a dispersion compensator 225, a third lens 227 to a fifth turning mirror, a sixth turning mirror 233, to a partial reflective mirror 235, and a reference mirror 237. The embodiment depicted in FIG. 2 is an MRO, a multiple reference OCT, in which the reference mirror 237 is mounted on a voice coil 239. Multiple reflections between the oscillating reference mirror 237 and the partial reflective mirror 235 generate multiple reference signals that extend the depth scanning range. An alternate embodiment using a swept source OCT system is depicted in FIG. 3.

As depicted in FIG. 2, turning mirrors 231 and 233 are on a stage 229, which moves in a lateral direction 240 in response to a conventional motor [not shown] such as voice coil motor, a squiggle motor, et cetera. Moving the stage 229 effectively alters the reference path length. Discussed further herein below, this path-length adjustment permits fine alignment of the axial length, useful for axially aligning depth scans of a target.

As can be seen in FIG. 2, the OCT photonic module 201 is attached to the frame 100 in such a manner that distance 207 between the OCT probe beam output port and the first 45 degree mirror 111 is such that the optical path length from the OCT beam-splitter 212 to the retina of the target eye [not shown] is substantially equivalent to the optical path length from the OCT beam-splitter 212 to the OCT reference mirror 237. The photonic module 201 being attached to the frame 100 in this manner ensures that the OCT photonic module is at least coarsely axially length aligned with the retina of the target eye. In alternate embodiments, where the target of interest is an eye component that is not the retina, the coarse axial length alignment of the photonic module is with respect to the target of interest.

The term "axially length aligned", for the purposes of this application, means that when an object or a portion of an object—that is to say, a target of interest—is "axially length aligned", the optical path length from the OCT beam-splitter to the target is substantially equivalent to the optical path length from the OCT beam-splitter to the OCT reference mirror. When these two path lengths are substantially equivalent, the object or portion of the object can be depth scanned by the OCT system. In the present invention, the object of interest is typically an eye, and a portion of the object is typically a component of an eye.

Referring again to FIG. 2, the distance 207 between the OCT probe beam output port and the first 45 degree mirror 111 is such the optical path is selected to coarsely axially length align the retina of the first target eye; additional fine axial length alignment is typically required to ensure appropriate OCT depth scans are acquired of the retina or other target of interest.

Fine axial length alignment is accomplished by dynamically adjusting an optical path length of the OCT photonic module 201. The dynamically adjusted optical path length is either the optical path length from the OCT beam-splitter 212 to the OCT reference mirror 237 or, alternatively, the OCT beam-splitter 212 to the retina [not shown]. It follows that in cases where the target is not the retina but another component of an eye, the distance is that of the OCT beam-splitter to the target of interest. Such fine alignment is achieved using feedback acquired by processing interference signals acquired by the OCT photonic module and is achieved by adjusting the lateral position of the stage 229. Those skilled in OCT operation and OCT signal processing can appreciate this without more description here. Thus, after fine axial length alignment is achieved, interference signals are acquired by the OCT photonic module and the acquired interference signals are processed to measure an aspect of the eye.

FIG. 3 depicts an alternate embodiment 300 of the invention, using a swept source 310, and a fixed reference mirror 337, rather than the MRO configuration depicted in FIG. 2. This embodiment provides the advantage of no moving parts, however, to be low cost, it requires the availability of a low cost swept source.

Figure 4:
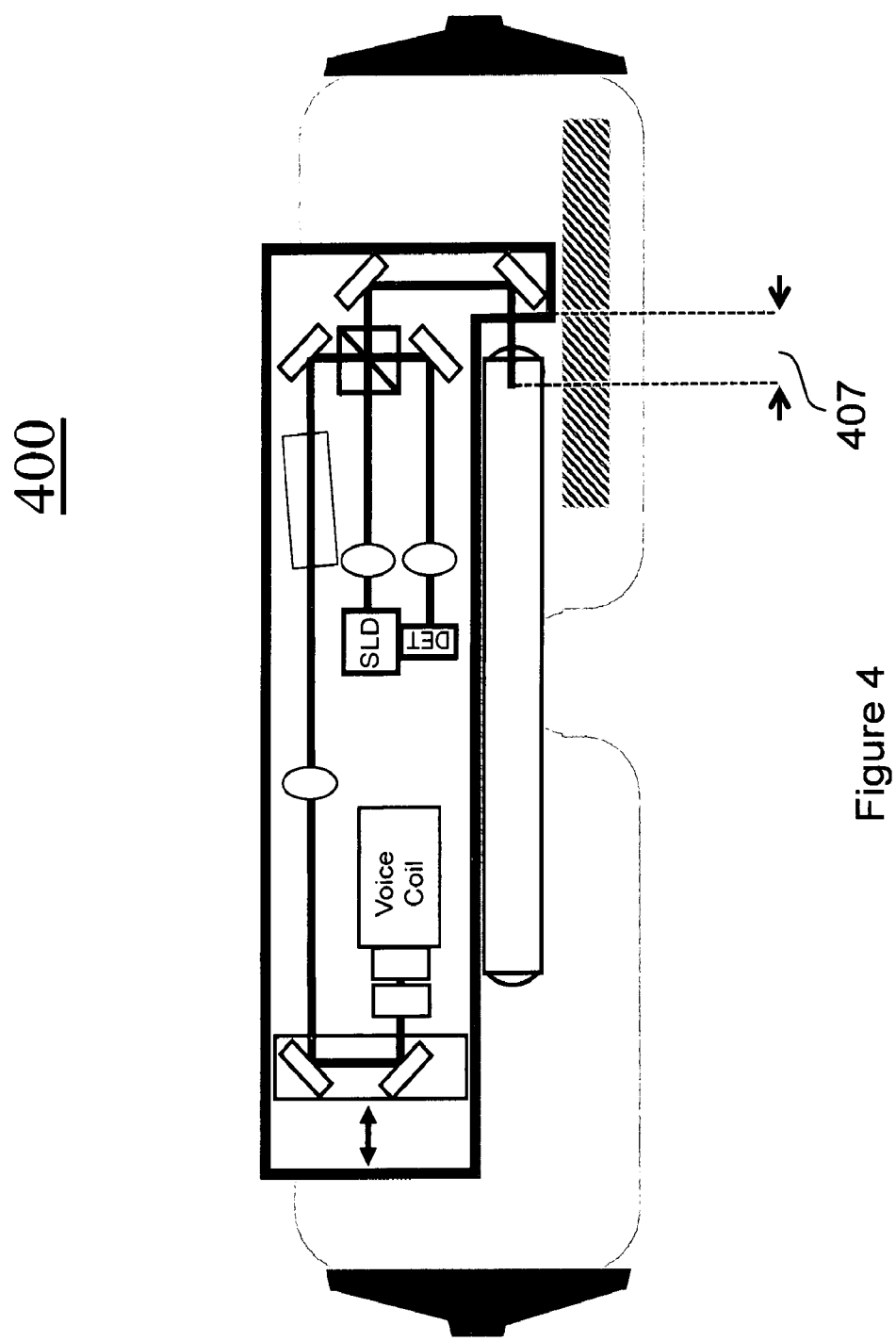
FIG. 4 depicts the frame and OCT photonic module of FIG. 2 where the photonic module is attached to the frame aligning the probe beam with the fellow (i.e.) second eye.

FIG. 4 depicts a second position of the embodiment depicted in FIG. 2. The OCT photonic module is attached to the frame in a manner that aligns its probe beam with the second eye of the individual as the target eye. If the depiction in FIG. 2 is thought of as right-oriented configuration for a right eye, then the depiction in FIG. 4 is left-oriented. The photonic module is the same as depicted in FIG. 2, and the majority of component numbers in to OCT photonic module have been omitted in FIG. 4. Referring to the left-oriented FIG. 4 it can be seen that the distance 407 between the OCT probe beam output port in the photonic module and the second 45 degree mirror 113 is such that the optical path is selected to coarsely axially length align the retina of this second target eye which may have a different axial length than the first target eye.

An appropriate selection of distance 407 of FIG. 4 and distance 207 of FIG. 2 and an appropriate locating mechanism that enables the OCT photonic module to be repeatedly accurately located in one of two locations and orientations with respect to the frame and enables the OCT photonic module to be attached and aligned with either eye of a subject, and enables the OCT photonic module to be coarsely axially length aligned with the retina of either eye.

In an embodiment of the invention, as described above, the OCT photonic module can be readily attachable to and detachable from a frame in at least two configurations, such that in a first configuration the OCT photonic module is aligned with a first eye and in a second configuration is aligned with the second eye, i.e. the fellow eye of the first eye.

It can be appreciated that the optional corrective lenses (117 and 119 of FIG. 1) correct for refractive error (if any) of either eye. Positioning of the corrective lenses may be other than as depicted, provided such lenses are in the path to the target eye. See for example FIG. 8C. The corrective lenses can be either fixed or variable and if variable can be either manually or electronically controlled. In alternate embodiments a single corrective lens, which may be a variable corrective lens, can be located on the OCT photonic module rather than the frame. This customizes the combination of frame and module for a single user.

In an alternate embodiment, the OCT photonic module is readily attachable to multiple different frames. In this embodiment, any user customization of corrective lenses would be in the user's frame, not necessarily in the OCT photonic module. In a further embodiment, the OCT photonic module is attached to a frame, and a switch enables measurements to be made on a first and a second eye without re-seating the module.

Figure 5B:
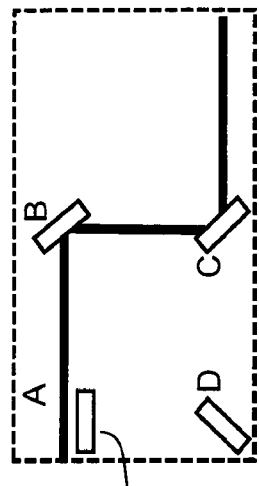
Figure 5C:
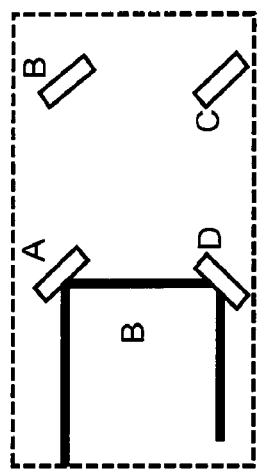
Figure 5A:
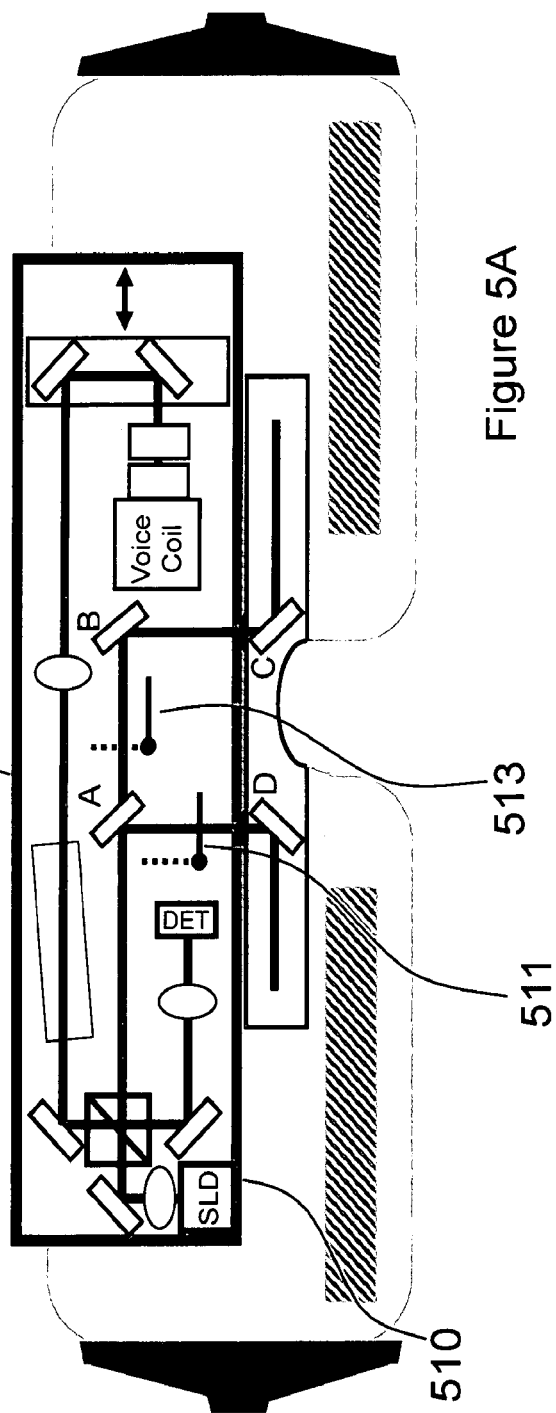

Referring now to FIG. 5A, an alternate embodiment is depicted providing for switchable OCT photonic beam without re-positioning the photonic module. By repositioning the source 510, and adding turning mirrors A, B, C, and D, and re-orientating the 45 degree mirrors (111 and 113 of FIG. 1), the OCT probe beam can be directed into both eyes simultaneously. In this embodiment the mirror A is a partial mirror that reflects substantially 50% and transmits substantially 50% of the OCT probe light. Electronically controlled beam stops 511 and 513 enable directing the probe beam into one or the other eye. FIG. 5A depicts the light path to mirror D being blocked, while the light path to mirror C is unblocked. Beam stops 511 and 513 also enable blocking light from entering both eyes, which could be used for safety purposes. Beam stops 511 and 513 are controllable to enable light to enter both eyes simultaneously, which could be used for fellow eye fixation or other purposes. In such an embodiment the re-oriented mirrors 111 and 113 of FIG. 1 are controlled so that one angularly scanned while the other is at a fixed orientation to achieve the desired fixation.

Many other embodiments are possible. For example, FIGS. 5B and 5C show another configuration of the mirrors A, B, C, and D. In this embodiment the alignment of the full mirror "A" is switchable. FIG. 5B depicts the switchable mirror 515 switched out of the path of the probe beam, enabling the probe beam to reach mirror C. FIG. 5C depicts the switchable mirror 515 switched into the path of the probe beam, enabling the probe beam to reach mirror D. It can be appreciated that a single unitary device, where the frame and photonic module are fixed as a unit, and the module not easily removable, is also an embodiment of this invention.

Seating the OCT photonic module on the frame is now described with respect to FIGS. 6, 6A and 6B, inclusive. In a preferred embodiment of the invention, asymmetric locating connectors, 602, 604 and 610, provide an appropriate locating mechanism that enables the OCT photonic module (shown in outline only) to be repeatedly accurately located in one of two locations and orientations with respect to the frame, by magnetically connecting 604 with 602 in FIG. 6A, and with 604 with 610 in FIG. 6B. It can be appreciated that one or more sets of magnetic locating connectors enable quick, easy and accurate attachment of the OCT photonic module 201 to a frame 100 in at least two configurations. The specific position of these magnetic locating connectors ensures that the OCT photonic module is at least coarsely aligned with one or the other eye. In the case of a module described with respect to FIG. 5, coarse lateral alignment with one eye is achieved by means of the magnetic locating connectors, while alignment with the other eye is achieved by the appropriate left to right location of mirror A and mirror D.

In the preferred embodiment, such magnetic locating connectors also provide electrical power, one or more data and control signal paths between the OCT photonic module and the frame. The use of two locating magnetic connectors that are asymmetric ensures correct orientation of the OCT photonic module. Additional, stabilizing connectors are depicted as 606 and 608 (with apertures for the light paths). It is should be noted that the element 103, i.e. the light guide or second component as depicted in FIG. 1, when configured as depicted in FIG. 6, provides a lateral surface for the stabilizing of the OCT photonic module on the frame, as well as providing connectivity.

It can be appreciated that the connectivity of the frame is configurable to wirelessly connect to a controlling device, such as a smart phone or a computer. The controlling device is configurable by, for example, a downloadable software application, enabling the Subject him or herself to make retinal measurements. Further data and scan results can be up-loaded and transmitted to a medical professional or to a medical file.

The invention also provides for scanning of the target, such as the retina of the eye, using angular adjustment of the mirrors in the frame. Referring again to FIG. 1B, modification of the angular orientation of the 45-degree mirrors 111, 113 in the second frame component 103 enables OCT scanning of the target. For example an angular deviation of +/−0.28 at a distance of 17 mm from the front of the eye achieves a +/−0.5 mm scan distance on the front of the eye and a +/−1 mm scan range at the posterior, i.e. the retina.

In addition, embodiments of the inventive device that include angularly adjustable mirrors provide a useful fixation function. Fixation, for ophthalmic purposes and as used herein, means the directing of an eye towards a fixed point. Fixation is useful in that it enables directing the OCT beam to a selected or targeted location or region of the retina. In this embodiment fixation can be achieved by having the angularly adjustable turning mirror oriented in a first direction to achieve a desired fixation direction for a first time period wherein fixation is achieved by the subject looking at the OCT probe beam and then rapidly switching the angularly adjustable turning mirror to be orientated in a second direction to achieve at least one depth scan at a selected target location that is different from the fixation orientation.

The angularly adjustable turning mirror can be repeatedly switched between the desired fixation direction and at least one target scan location to achieve a measurement at a desired location. The angularly adjustable turning mirror may be repeatedly orientated in a set of directions that form a pattern and fixation can be achieved by having the Subject look at the center of the pattern.

Figure 7:
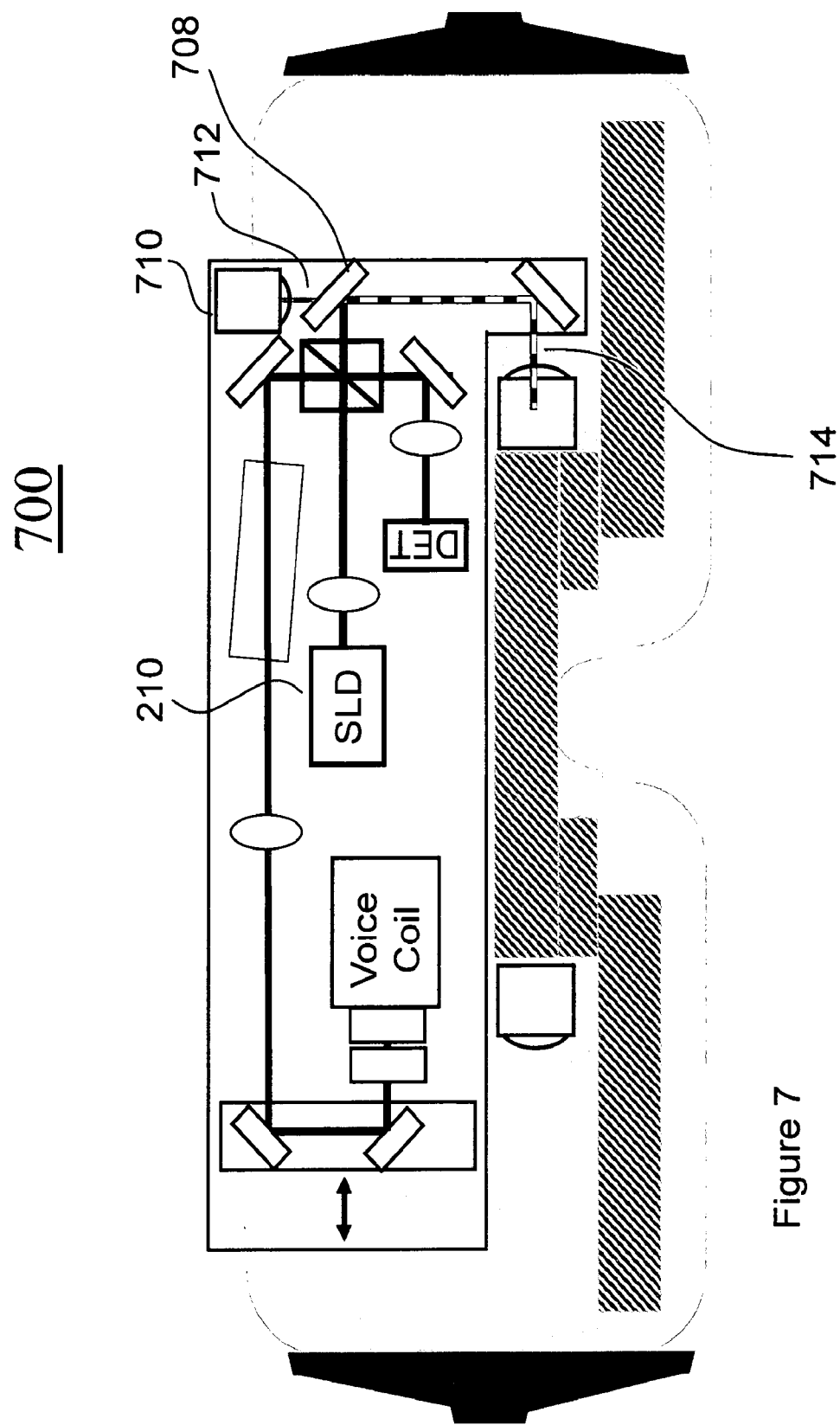
FIG. 7 depicts an embodiment providing an additional visible fixation beam generated by an LED, or other visible light source, that is intermittently turned on when an angularly scanning mirror is directed at an orientation that will provide the desired fixation.

In an alternate embodiment a selected region of the eye is scanned by operating the angularly adjustable turning mirror in a scanning mode. In this embodiment fixation is achieved by the use of an additional visible beam and by intermittently adjusting the angle of the turning mirror such that it is oriented in a desired fixation direction for a first period of time and turning on the visible beam wherein fixation is achieved by the subject looking at the visible beam. FIG. 7 depicts an OCT probe module according to the invention further providing an additional visible fixation beam 712 generated by an LED 710, or other visible light source, that is intermittently turned on when an angularly scanning mirror is directed at an orientation that will provide the desired fixation. An LED 710, such as a green LED, is collimated and is combined with and made collinear with the OCT probe beam by means of a dichroic mirror 708. [059] The green fixation LED is turned on for a short duration when the dynamically controlled turning mirrors 111 or 113 of FIG. 1B points in a preselected fixation direction, causing the Subject under test to fixate the target eye in that direction. When the green LED is off, the dynamically controlled turning mirror directs the OCT probe beam in the direction from which depth scan information is desired. The co-propagating collinear fixation beam and OCT probe beam are depicted as 714. In general a "fixation beam" is referred to as a "visible fixation beam".

At times other than the first period of time when fixation is achieved, scanning is achieved by systematically angularly adjusting one of the turning mirrors 111 or 113 of FIG. 1B to cause the probe beam of the OCT photonic module to scan a selected region of the retina. The interference signals that are acquired by the OCT photonic module while a) the OCT photonic module is accurately axially length aligned with the retina of the eye and b) while the probe beam is systematically moved by the angularly adjusting turning mirror, are processed to output data representing a scan of a region of the retina of an eye. The same holds true for targets other than the retina.

In other embodiments, rather than acquiring interference signals from the retinal region of the eye, aspects of other components of the eye are analyzed. It can be appreciated that the target component to be analyzed includes eye components of interest such as the cornea, the anterior chamber or the crystalline lens the eye. In typical ophthalmic applications, the aspect of the target component to be measured is the thickness of the target component.

The angularly scanning approach is further illustrated in FIG. 8A which depicts a portion of the second frame component 103 of FIG. 1. In FIG. 8A the 45 degree mirror is a one or two dimensional angularly scanning mirror which in a first scan position 811 is at a 45 degree angle and directs the incoming probe beam 813 through the nominal center of the cornea 817 and pupil to a location 815 that is in the region of the center of the retina 817 of the eye 819. The angularly scanning mirror is also depicted in a second scan position 821, depicted as a dashed line. In this position the probe beam 813 is directed to an off-center point 823 on the cornea 817, through the pupil 825 to a location 827 on the retina that has a lateral offset from the center region 815.

An alternate embodiment that enables larger scan angles is depicted in FIG. 8B where there is also linear translation capability of the angularly adjustable mirror 829. This is depicted by the dashed line 831, which represents the position of the mirror 829 when angularly adjusted and translated to the right. The combination of linear translation in conjunction with angular scanning enables keeping the beam substantially centered on the pupil while scanning greater regions of the retina without the requirement of dilating the pupil. The scanning and translation mechanisms are implemented using MEMS or electro-mechanical (voice-coil like) mechanisms. Herein the term "positionally adjusting" includes aligning by angular adjustment or aligning by means of linear translation or by a combination of angular adjustment and linear translation.

Referring again to FIG. 8B, in some embodiments one or more cameras are mounted on the device and acquire an image of the eye. In some embodiments one or more cameras acquire an image of the eye that includes an image of the probe beam by means of light scattered at the cornea. This image data enables manual or automatic alignment of the probe beam with respect to the eye by means of the angularly adjustable mirrors and optionally also by means of the linear translation. In some embodiments one or more plenoptic cameras (also sometimes referred to as light field or field of light cameras) are used to acquire more image data from the eye. FIG. 8C also depicts a portion of the second frame component 103 and depicts the corrective lens 837 in a different location to that depicted in FIGS. 8A and 8B. In the embodiment depicted in FIG. 5 other locations for corrective lenses are above the mirrors D and C (depicted as black curved regions).

Although the OCT systems illustrated are a multiple reference time domain OCT system and a swept source OCT system, it can be appreciated that alternate embodiments use other OCT systems such as conventional time domain OCT systems and spectral Fourier domain OCT systems. In some embodiments an OCT system external to the photonic module could be fiber coupled to the photonic module. This arrangement enables availing of the advantages of the low cost custom frame while using expensive very high performance OCT systems.

FIG. 9A depicts such an arrangement where an external OCT system is fiber-coupled to the photonic module 901 by means of a fiber-coupler 903. In the example depicted in FIG. 5A, the module 901 routes the OCT probe beam to one, the other, or both eyes (as described earlier). The returning OCT signals are captured and routed back along the same fiber to the OCT system.

An alternate embodiment is depicted in FIG. 9B where an external swept source is fiber-coupled to the photonic module 905 by means of a fiber-coupler 907. In this example the photonic module 905 contains the OCT interferometer including the reference mirror 909 for the swept source.

The photonic module illustrated uses a single OCT beam. In alternate embodiments, the invention includes an array of SLDs (super luminescent diodes) or, alternatively, a single high power SLD, is used and separated into multiple beams by means of a holographic optical element. The resulting multiple beams are directable at different angles so as to probe different locations on the retina. The resulting multiple interference signals are focusable onto a detector array by means of a lens array, providing a set of depth scans at an array of locations simultaneously. This effectively enables measurements to be made in less time.

Other examples will be apparent to persons skilled in the art. The scope of this invention is determined by reference to the specification, the drawings and the appended claims, along with the full scope of equivalents as applied thereto.

The invention claimed is:

1. A device, said device comprising:
   a frame, a User-customizable unit, and a multiple reference optical coherence tomography system, where
   said frame is mountable on a User head, said head having at least one eye to be tested, so that said optical coherent tomography system and said User-customizable unit, mounted on said frame permits probe radiation to enter a first eye and a second eye; wherein
   said User-customizable unit is of a preselected length according to inter-pupillary distance of said User, and where said unit is mounted on said frame in a first position such that
   a first turning mirror in said unit is positioned to direct probe beam of an optical coherent tomography system into said first eye; and a second turning mirror in said unit is positioned to direct said probe beam into said second eye; and wherein
   said optical coherence tomography system is a multiple reference optical coherence tomography system, and is comprised of:
   a radiation source and in the path of said radiation
   a collimating lens, said lens directing radiation to a beam splitter, said beam splitter splitting beam into a reference beam and a probe beam,
   wherein said reference beam is directed to turning mirror, and then directed
   through a with dispersion compensator, through a lens and
   through a pair of turning mirrors on a translational stage, said translational stage moving laterally left and right to compensate for axial length of said eye under test, through a partial mirror and to an oscillating
   reference mirror mounted on a voice coil, such that multiple reflections between the oscillating reference mirror and said partial reflective mirror generate multiple reference signals that extend the depth scanning range;
   and wherein said probe beam is directed from beam splitter to a first turning mirror and a second turning mirror sending probe beam into User-customizable unit, where said beam is directed into said first eye; and
   returning probe beam radiation is directed by a first turning mirror and a second turning mirror back to said beam splitter, where returning probe beam is directed to a mirror and,
   in combination with returning reference beam radiation, directed to a lens and to a detector such that multiple interference signals are generated, and
   wherein said optical; coherent tomography system unit is mountable in a second position such that said probe radiation is directed by said second turning mirror in said custom User unit to said second eye, such that
   data from said first eye and said second eye is output, said data pertinent to eye health.

2. A device, said device comprising:
   a frame, a User-customizable unit, and a multiple reference optical coherence tomography system, where
   said frame is mountable on a User head, said head having at least one eye to be tested, so that said optical coherent tomography system and said User-customizable unit mounted on said frame permit probe radiation to enter a first and a second User eye;
   said User-customizable unit is of a preselected length according to inter-pupillary distance of said User, and wherein said unit is
   mounted on said frame in aposition such that a first turning mirror in said unit is positioned to direct probe beam of an optical coherent tomography system into said first eye; and a second turning mirror in said unit is positioned to direct said probe beam into said second eye; and wherein said optical coherence tomography system is a multiple reference optical coherence tomography system, and is comprised of:

a radiation source and in the path of said radiation, a collimating lens, said lens directing radiation to a turning mirror and then to a beam splitter, said beam splitter splitting beam into a reference beam and a probe beam, wherein said reference beam is directed to turning mirror, then directed through a with dispersion compensator, through a lens, through a pair of turning mirrors on a translational stage, said translational stage moving laterally left and right to compensate for axial length, through a partial mirror and an oscillating reference mirror mounted on a voice coil, such that multiple reflections between the oscillating reference mirror and said partial reflective mirror generate multiple reference signals that extend the depth scanning range;

and wherein said probe beam is directed through said beam splitter, said beam splitter sending fifty percent of source radiation to one or more first turning mirrors, and subsequently to said first eye under test, and sending fifty percent of source radiation to one or more second turning mirrors, and subsequently to said second eye under test, wherein the beam between said first turning mirrors is controllable by a first blocking switch, which blocks the probe beam, and wherein the beam between said second turning mirrors is controllable by a second blocking switch, so that the probe beam is directable to either of said two eyes without adjusting said frame or said optical coherence tomography system or said User-customizable unit;

and wherein returning; probe beam radiation is directed back to said beam splitter, and then directed to a mirror in the optical path, and, in combination with returning reference beam radiation, directed to a lens and a detector, wherein multiple; interference signals are generated, which signals are processed and data output, said datapertinent to eye health.

3. The device of claim 2, wherein said optical coherent tomography system is a conventional time domain optical coherence tomography system.

\* \* \* \* \*